(12) United States Patent
Qiu et al.

(10) Patent No.: US 9,109,440 B2
(45) Date of Patent: Aug. 18, 2015

(54) ESTIMATING DIFFUSION COEFFICIENT FOR A RESERVOIR STIMULATION FLUID

(71) Applicant: SCHLUMBERGER TECHNOLOGY CORPORATION, Sugar Land, TX (US)

(72) Inventors: Xiangdong Qiu, Al-Khobar (SA); Frank F. Chang, Al-Khobar (SA)

(73) Assignee: Schlumberger Technology Corporation, Sugar Land, TX (US)

( * ) Notice: Subject to any disclaimer, the term of this patent is extended or adjusted under 35 U.S.C. 154(b) by 170 days.

(21) Appl. No.: 13/972,669

(22) Filed: Aug. 21, 2013

(65) Prior Publication Data

US 2014/0057356 A1 Feb. 27, 2014

Related U.S. Application Data

(60) Provisional application No. 61/692,112, filed on Aug. 22, 2012.

(51) Int. Cl.
| | | |
|---|---|---|
| *G01N 33/24* | (2006.01) | |
| *E21B 43/16* | (2006.01) | |
| *E21B 43/25* | (2006.01) | |
| *C09K 8/72* | (2006.01) | |

(52) U.S. Cl.
CPC . *E21B 43/16* (2013.01); *C09K 8/72* (2013.01); *E21B 43/25* (2013.01); *G01N 33/24* (2013.01)

(58) Field of Classification Search
USPC .......................................... 436/25, 29, 31–34
See application file for complete search history.

(56) References Cited

U.S. PATENT DOCUMENTS

| | | | |
|---|---|---|---|
| 2006/0184346 A1* | 8/2006 | Panga et al. ....................... 703/9 |
| 2009/0209439 A1* | 8/2009 | Qiu et al. ....................... 507/267 |
| 2012/0202720 A1* | 8/2012 | de Wolf et al. ................ 507/241 |
| 2014/0212006 A1* | 7/2014 | Zhao et al. ..................... 382/109 |

OTHER PUBLICATIONS

Fredd, C. N. et al, Journal of Colloid and Interface Science 1998, 204, 187-197.*
Gautelier, M. et al, Chemical Geology 1999, 157, 13-26.*
Al-Khaldi, M. H. et al, Chemical Engineering Science 2007, 62, 5880-5896.*
Taylor K. C. et al, Journal of Canadian Petroleum Technology 2009, 48, 66-70.*
Chang, F. et al, KSG 2011, 20 pages.*
Boomer, et al., "Rotating Disk Apparatus for Reaction Rate Studies in Corrosive Liquid Environments", The Review of Scientific Instruments, vol. 43 (2), Feb. 1972, pp. 225-229.
Levich, V.G., "Physicochemical Hydrodynamics", Prentice-Hall, Englewood Cliffs, N.J., 1962, p. 69.

(Continued)

*Primary Examiner* — Arlen Soderquist
(74) *Attorney, Agent, or Firm* — Bridget M. Laffey

(57) ABSTRACT

The subject disclosure relates to matrix acidizing. More specifically, systems and methods are described for estimating a diffusion coefficient for an acid fluid used to stimulate a subterranean reservoir wherein a spent acid is formulated that includes one or more by-products of the reaction between the fluid and rock. A rock sample, such as in the form of a rotating disk is exposed to spent acid under elevated pressure and temperature conditions while the fluid is sampled and analyzed. A diffusion coefficient for the spend acid is estimated.

15 Claims, 7 Drawing Sheets

(56) References Cited

OTHER PUBLICATIONS

Qiu, et al., "Revisiting Reaction Kinetics and Wormholing Phenomena During Carbonate Acidizing", IPTC-17285—International Petroleum Technology Conference, Doha, Qatar, Jan. 20-22, 2014, pp. 1-15.

Qui, et al., "Quantitative Modeling of Acid Wormholing in Carbonates—What Are the Gaps to Bridge", SPE 164245—SPE Middle East Oil and Gas Show and Conference, Manama, Bahrain, Mar. 10-13, 2013, pp. 1-15.

Sparrow, et al., "Mass Transfer, Flow, and Heat Transfer About a Rotating Disk", Journal of Heat Transfer, vol. 82 (4), Nov. 1, 1960, pp. 294-302.

Weishu, et al., "Method for Quantitative Prediction of Matrix Acidizing Treatment Outcomes", U.S. Appl. No. 13/752,859, filed Jan. 29, 2013, 46 pages.

* cited by examiner

US 9,109,440 B2

ESTIMATING DIFFUSION COEFFICIENT FOR A RESERVOIR STIMULATION FLUID

CROSS REFERENCE TO RELATED APPLICATION(S)

This application claims the benefit of U.S. Provisional Patent Application Ser. No. 61/692,112 filed Aug. 22, 2012, which is incorporated herein by reference in its entirety.

FIELD

The subject disclosure generally relates to matrix acidizing well stimulation procedures. More particularly, the subject disclosure relates to systems and methods for estimating diffusion coefficients and/or reaction rates between partially spent acid and carbonate rock.

BACKGROUND

Carbonate matrix acidizing extends well effective drainage by dissolving rock and forming conductive channels (wormholes) from the wellbore. Wormholing is a dynamic process that involves a balance between the acid injection rate and reaction rate. A rotating disk is increasingly being applied in the laboratory for studying reactions between fluids and solid surfaces. The acid reaction kinetics of an acid reaction with a carbonate involves three phases: (1) the transport of $H^+$ ions from the bulk solution to the surface of a carbonate; (2) the reaction of $H^+$/carbonates takes place on the surface of the carbonate; and (3) the transport of the reaction products from the carbonate surface to the bulk solution. The slowest phase controls the global reaction rate.

Mass transfer limits the reaction of hydrochloric acid with carbonate rock under reservoir conditions. The mass transfer coefficient determines how fast the rock is dissolved by the acid and therefore the wormhole profile and penetration during matrix acid stimulation. The mass transfer coefficient is controlled by: (1) the fluid injection rate; and (2) the diffusion coefficient of the acid. While injection rate is easily known from the job execution, the diffusion coefficient is intrinsically a hidden parameter of the fluid and reaction conditions and is measured experimentally. Currently, the diffusion coefficient of fresh acid is used to calculate the process of wormholing. The use of a fresh acid diffusion coefficient is adequate for wormholing phenomena near the wellbore, but as the wellbore penetrates deep into the formation, the tip of the wormhole contains predominantly spent acid. Therefore, the use of a diffusion coefficient based on fresh acid may overestimate the dissolution rate.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

According to some embodiments, a method is described for estimating a diffusion coefficient for a stimulation fluid used to stimulate a subterranean reservoir rock by partially dissolving the rock. The method includes generating a partially spent stimulation fluid including a stimulation fluid used to stimulate the subterranean reservoir rock and one or more reaction by-products. The reaction by-products are of a type produced during reaction of the stimulation fluid with the reservoir rock. In a sealed chamber, a sample of reactant material is exposed to the partially spent stimulation fluid under elevated pressure conditions such that the reactant material reacts with the partially spent stimulation fluid. Properties of the partially spent stimulation fluid are then measured after at least some of the reactant material has reacted with the partially spent stimulation fluid and estimating therefrom a diffusion coefficient for the stimulation fluid under partially spent downhole conditions.

According to some embodiments, the reservoir rock is a carbonate reservoir rock and the reaction by-products include: dissolved $CO_2$; calcium ions; and/or magnesium ions. The sample of reactant material is a solid rotating disk having a material found in the subterranean reservoir rock. In the case of carbonate reservoirs, the solid rotating disk can be a non-porous material such as marble, while the stimulation fluid is hydrochloric acid. According to some embodiments, the reaction with the rotating disk is carried out at elevated temperature and pressure conditions that correspond to conditions expected in the subterranean reservoir rock. According to some embodiments, the pressure is at least 1000 psi, and in other embodiments is at least 3000 psi. According to some embodiments, the method further includes estimating a reaction rate and/or modeling wormhole morphology based at least in part on the estimated diffusion coefficient. According to some embodiments, the diffusion coefficient is estimated by sampling the partially spent stimulation fluid at intervals while the reactant material reacts with the partially spent stimulation fluid.

According to some embodiments, a system is described for estimating a diffusion coefficient for a stimulation fluid used to stimulate a subterranean reservoir rock by at least partially dissolving the rock. The system includes: a sealed reaction vessel configured to expose a partially spent stimulation fluid to a sample of reactant material under elevated pressure conditions such that the reactant material reacts with the partially spent stimulation fluid. The partially spent stimulation fluid is pre-formulated to include one or more reaction by-products being of a type produced during reaction of the stimulation fluid with the reservoir rock. The system also includes a data acquisition and processing system configured to measure properties of the partially spent stimulation fluid after at least some of the reactant material has reacted with the partially spent stimulation fluid and estimate therefrom a diffusion coefficient for the stimulation fluid under partially spent downhole conditions. According to some embodiments, the system also includes a separate vessel configured to generate the partially spent stimulation fluid by reacting a fresh acid with material of a type found in the subterranean reservoir rock.

Further features and advantages of the subject disclosure will become more readily apparent from the following detailed description when taken in conjunction with the accompanying drawings.

BRIEF DESCRIPTION OF THE DRAWINGS

The subject disclosure is further described in the detailed description which follows, in reference to the noted plurality of drawings by way of non-limiting examples of embodiments of the subject disclosure, in which like reference numerals represent similar parts throughout the several views of the drawings, and wherein.

DETAILED DESCRIPTION

Figure 1:
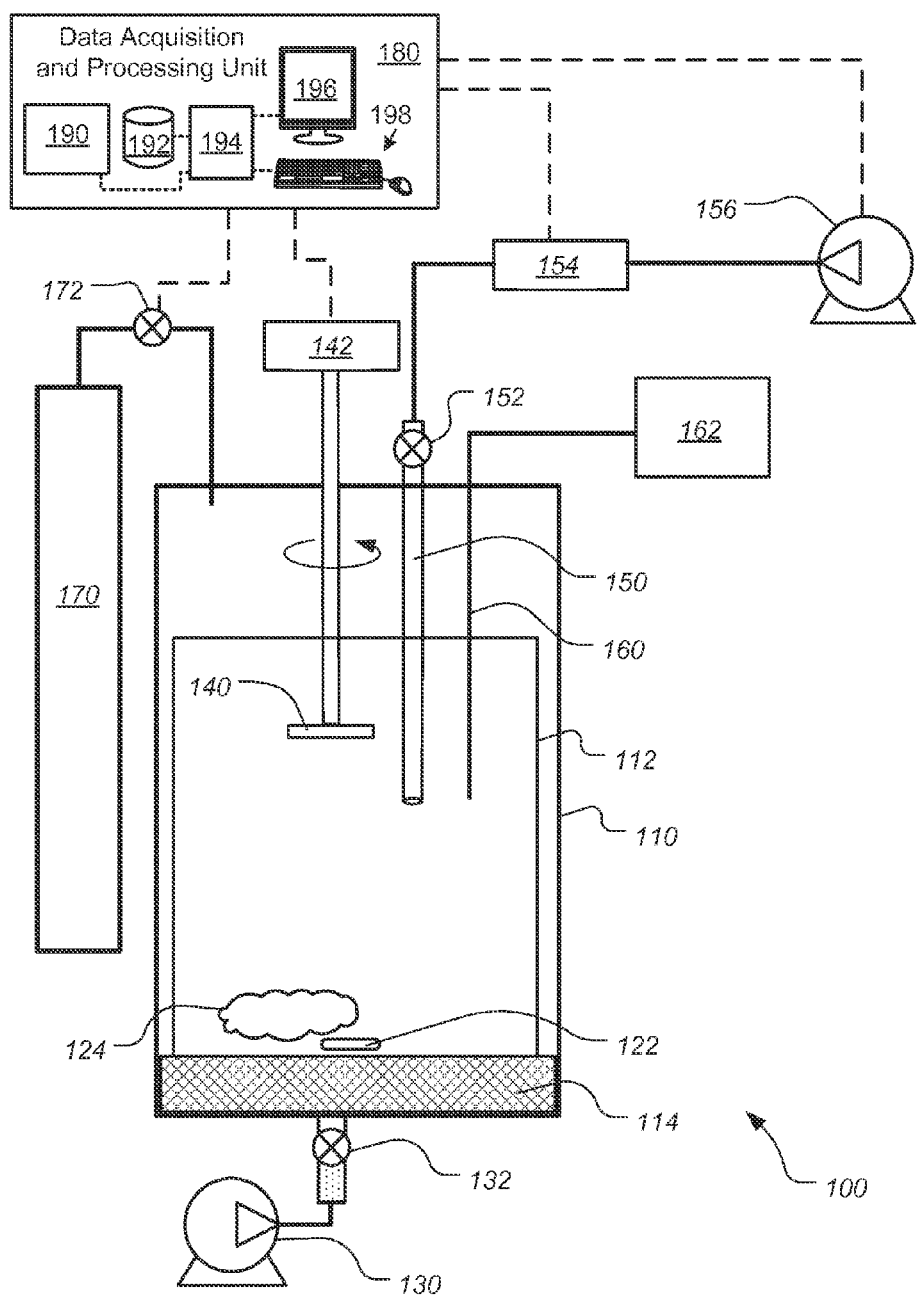
FIGS. 1-3 are block diagrams illustrating operational aspects of a system for estimating diffusion coefficients for a reservoir stimulation fluid, according to some embodiments.

The particulars shown herein are by way of example and for purposes of illustrative discussion of the embodiments of the subject disclosure only and are presented in the cause of providing what is believed to be the most useful and readily understood description of the principles and conceptual aspects of the subject disclosure. In this regard, no attempt is made to show structural details in more detail than is necessary for the fundamental understanding of the subject disclosure, the description taken with the drawings making apparent to those skilled in the art how the several forms of the subject disclosure may be embodied in practice. Furthermore, like reference numbers and designations in the various drawings indicate like elements.

Conventional wormhole propagation models largely ignore the impact of reaction products. It has been found that in order to achieve quantitative predictability of wormhole penetration during an acidizing treatment, the effects of reaction products on reaction kinetics should be better understood. Generally, the acid injection rate is well defined where injection profiles can be controlled, whereas the reaction rate can be difficult to obtain due to its complex dependency on interstitial velocity, fluid composition, rock surface properties etc. When implemented in a job design, errors can result in treatment fluid schedule, rate, and volume.

According to some embodiments, the diffusion coefficient is used in order to properly quantify the acid penetration deep into the formation. According to some embodiments, a rotating disk apparatus is used to measure the diffusion coefficient for fresh HCl. During the reaction between the HCl and calcite, the acid concentrations decrease while calcium ions and $CO_2$ are produced. It has been found that temperature and the concentration of the reaction products of HCl/carbonate impact the diffusion coefficient. The impact from the reaction products (count ions, and especially $CO_2$) is quantified, according to some embodiments. The amount of $CO_2$ produced from acid/carbonate reaction is known. However, it has been found that the amount of $CO_2$ that will stay in the solution to form $H_2CO_3$ is mainly dependent on the surrounding pressure and temperature. According to some embodiments, therefore, acid/carbonate reaction rate studies are formulated using in-situ "spent" acid. As used herein, the term "spent acid" refers to acid that has not only been weakened due to reaction but also contains one or more of the reaction by-products, which have been found to effect the reaction rates.

According to some embodiments, a controllable modified rotating disk apparatus is used to study the diffusion coefficient of the true spent acid/carbonate. A first process is used to generate a "true" spent acid formulation, which uses the reaction mechanism of acids and carbonates. The quantities of reactants (acids and carbonates) can be precisely determined by the stoichiometric calculation. The reaction for generating the spent acid takes place in a reaction vessel at a controlled pressure and temperature. Sufficient time and mixing are used to ensure the reaction is complete. In a second process, the in-situ spent acid prepared in the first process is placed in a modified reaction vessel, such that a rotating disk is immersed in the "true" spent acid while the disk is rotated at a desired RPM (Revolutions Per Minute). According to some embodiments, the described reaction between the rotating disk and spent acid takes place in the same reaction vessel and at a same temperature and pressure as the first process. According to other embodiments, separate vessels are used for the first and second processes.

Figure 2:
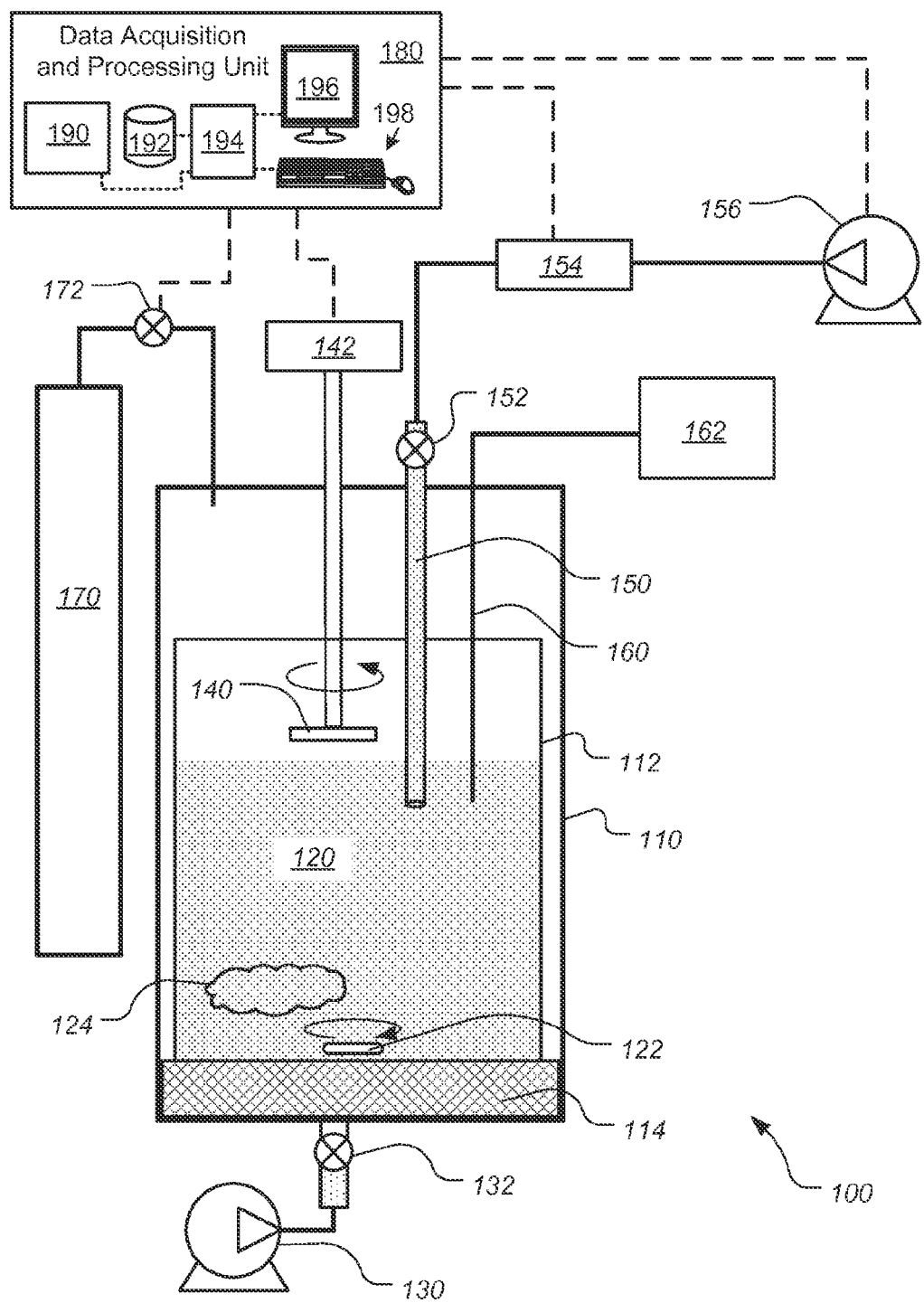
Figure 3:
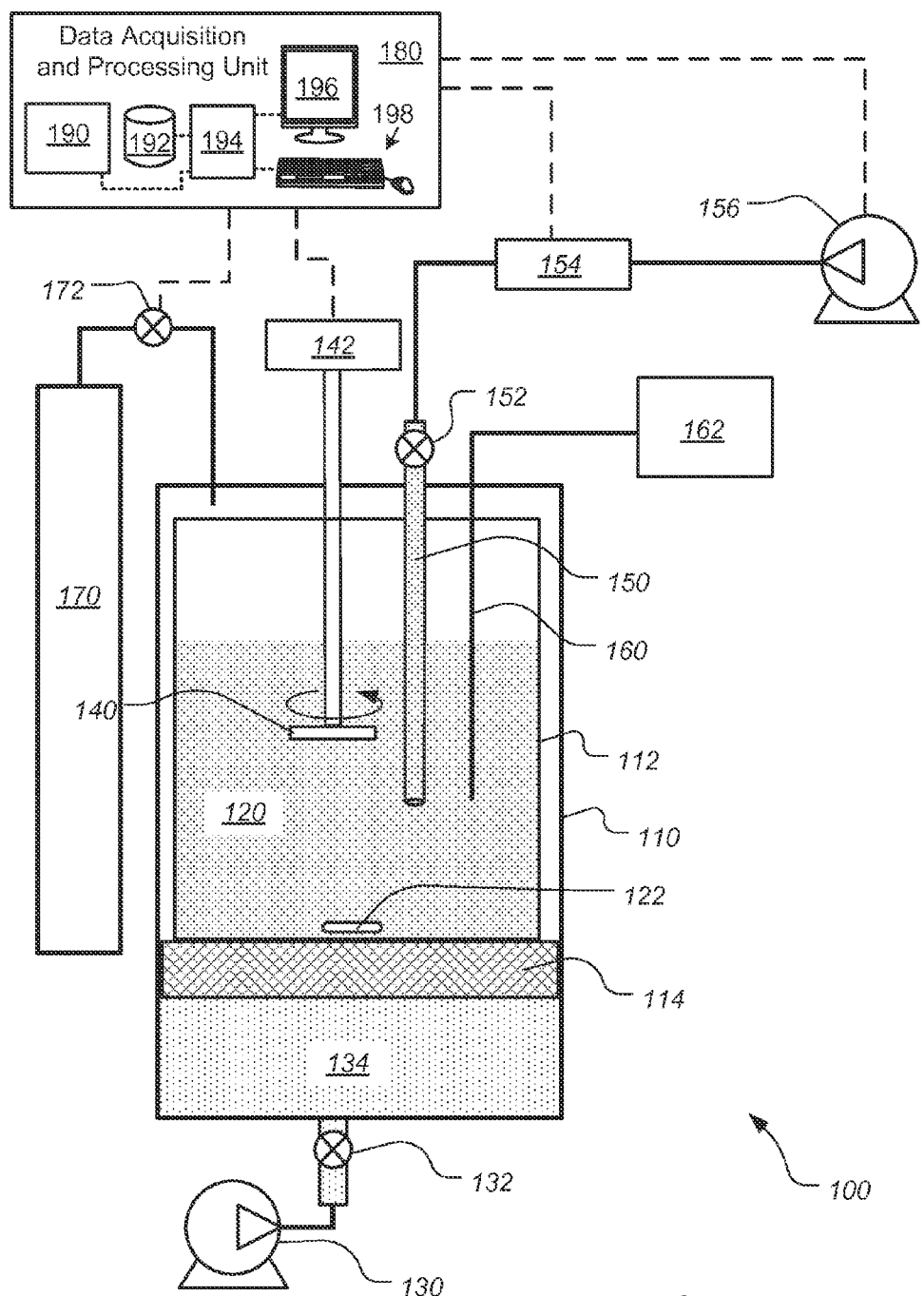

FIGS. 1-3 are block diagrams illustrating operational aspects of a system for estimating diffusion coefficients for a reservoir stimulation fluid, according to some embodiments. In FIG. 1, testing system 100 includes a reaction vessel 110 for holding the acid (or other stimulation fluid being tested) while it reacts with the material on rotating disk 140. According to some embodiments, such as shown in FIG. 1, the reaction vessel 110 includes a liner made of suitable material, such as Teflon, which can be raised under the actuation of piston 114 which can also be made of a material such as Teflon. The piston 114 is controlled via pump 130 and valve 132. According to some embodiments, pump 130 is a syringe pump such as made by Teledyne Isco, which pumps water that acts to raise piston 114. The system 100 also includes a gas booster system that includes a gas source 170 and valve 172 for pressurizing the reaction vessel 110. Temperature of the vessel 110 is measured and controlled by thermocouple 160 and heating system 162 which can also include a heating jacket (not shown). An acid reservoir 154 holds fresh acid (or other stimulation fluid). Acid is injected and sampled through sampling tube 150 via valve 152, accumulator/reservoir 154 and pump 156. Rotating disk 140 is rotated using motor 142. A magnetic drive assembly (not shown) spins magnetic pin 122 for mixing within vessel 110. In addition, a data acquisition system is established to closely monitor the temperature and pressure inside the reaction vessel. Also shown in FIG. 1 is data acquisition and processing unit 180, which according to some embodiments includes a central processing system 194, a storage system 192, communications and input/output modules 190, a user display 196 and a user input system 198. The data acquisition and processing unit 180 is used to monitor and control pressure, temperature, and to acquire and analyze data from sampling tube 150. Additionally, according to some embodiments, unit 180 is configured to control pumps 130 and 156 as well as valves 132, 152 and 172.

In the case of evaluating an HCl acid fluid for stimulating a carbonate reservoir, according to some embodiments, disk 140 is made of pure marble which has the benefit of being 100% limestone and having no porosity. According to other embodiments, other carbonate rocks may be used, having a suitable diameter and thickness.

According to some embodiments, a testing procedure is started in FIG. 1 with a measured amount of carbonate powder 124 in liner 112 of vessel 110. The piston 114 is positioned in the bottom of the reaction vessel 110. The disk 140 is mounted on a spindle (for example using heat-shrink Teflon tubing, such that only the lower face of disk 140 can be exposed to acid in vessel 110. According to some embodiments, a new disk 140 is used for each experiment.

The reaction vessel 110 is pressurized using system backpressure gas source 170 (such as nitrogen) and valve 172 to a desired level, and the reaction vessel 110 and the acid reservoir 154 are heated to the same desired temperature. According to some embodiments, the pressure and temperature is matched to the conditions expected in the reservoir stimulation application. According to some embodiments, a pressure of at least 1000 psi is used. According to some embodiments, pressures of 3000 psi, 5000 psi and even 10,000 psi are used for carrying out the tests.

After the pressure and temperature stabilizes, the rotation of disk 140 is started and fresh acid is injected from the reservoir to the reaction vessel 110 by pressurizing the acid reservoir 154 to a higher pressure than the pressure in the reaction vessel 110, using nitrogen gas from pump 156.

FIG. 2 depicts the acid 120 reacting with the carbonate powder 124 to formulate a spent acid, which contains by-products of the reaction with carbonate 124, and is under the pressure and temperature conditions of vessel 110. The injected acid reaction with the carbonate powder 110 is aided by mixing using the magnetic pin 122.

After the reaction between the carbonate powder 124 and the injected acid 120 is complete, the concentration of acid and the produced counter ions are as expected. In addition, a partial amount of $CO_2$ is dissolved in the solution due to the initially applied backpressure. In other words, the spent acid is in-situ "true" spent acid, which is ready for the next stage of testing. The pump 130 starts to inject water at a relatively high flow rate. The displaced water pushes the piston 114 up, and therefore the spent acid level 120 will increase until the rotating disk 140 is completely immersed under the spent acid 120 as depicted in FIG. 3.

Time recording is started once the rotating disk 140 is completely immersed into the spent acid 120. According to one experimental procedure, effluent samples are extracted approximately every minute for a period of five minutes and each sample is about 10 ml in volume. The sampling tubing 150 is preferably purged prior to collecting each sample. Volumes are collected, recorded and discarded. $Ca^{2+}$ concentration is recorded based on the remaining volume of acid 120 in the reaction vessel 110 at the time of sampling. The $Ca^{2+}$ ion concentration in each collected sample is analyzed for later calculation of the diffusion coefficient.

According to some embodiments, to quantify the amount of carbonate powder and acids needed to formulate the required spent acid, the following stoichiometric calculation may be used. For preparation of 1 L of 10% "true" spent acid, the initial concentration of HCl is assumed to be 15%. This concentration of HCl reacts with calcium carbonate until the concentration reduces to HCl 10%. The difference between a 10% spent HCl and a 10% fresh HCl is that the spent HCl contains HCl/$CaCO_3$ reaction product-$CaCl_2$ and $CO_2$. The stoichiometric calculation of $CaCO_3$ reacting with HCl solution is illustrated as follows: 15% HCl=4.4174 mol/L, 10% HCl=2.8767 mol/L, 4.4174−2.8767=1.5407 mol/L. Since 2 mole of HCl dissolves 1 mole of $CaCO_3$, 1 L of 15% HCl spending to 10% HCl should react with 0.77035 mole of $CaCO_3$. 77.035 g of calcium carbonate powder is placed in liner 112 of vessel 110 (as shown in FIG. 1).

Figure 4:
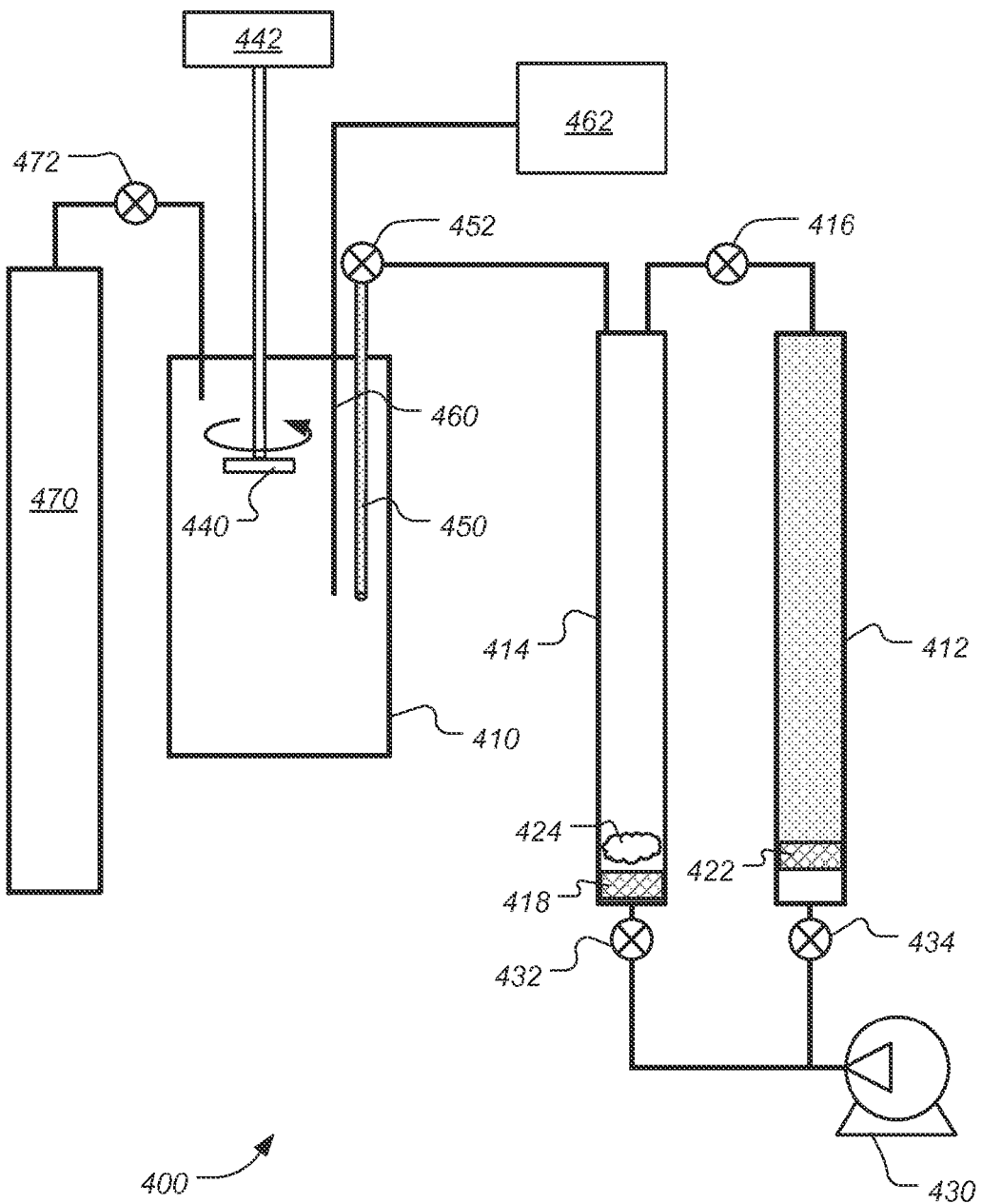
FIGS. 4-6 are block diagrams illustrating operational aspects of a system for estimating diffusion coefficients for a reservoir stimulation fluid, according to some other embodiments.
Figure 5:
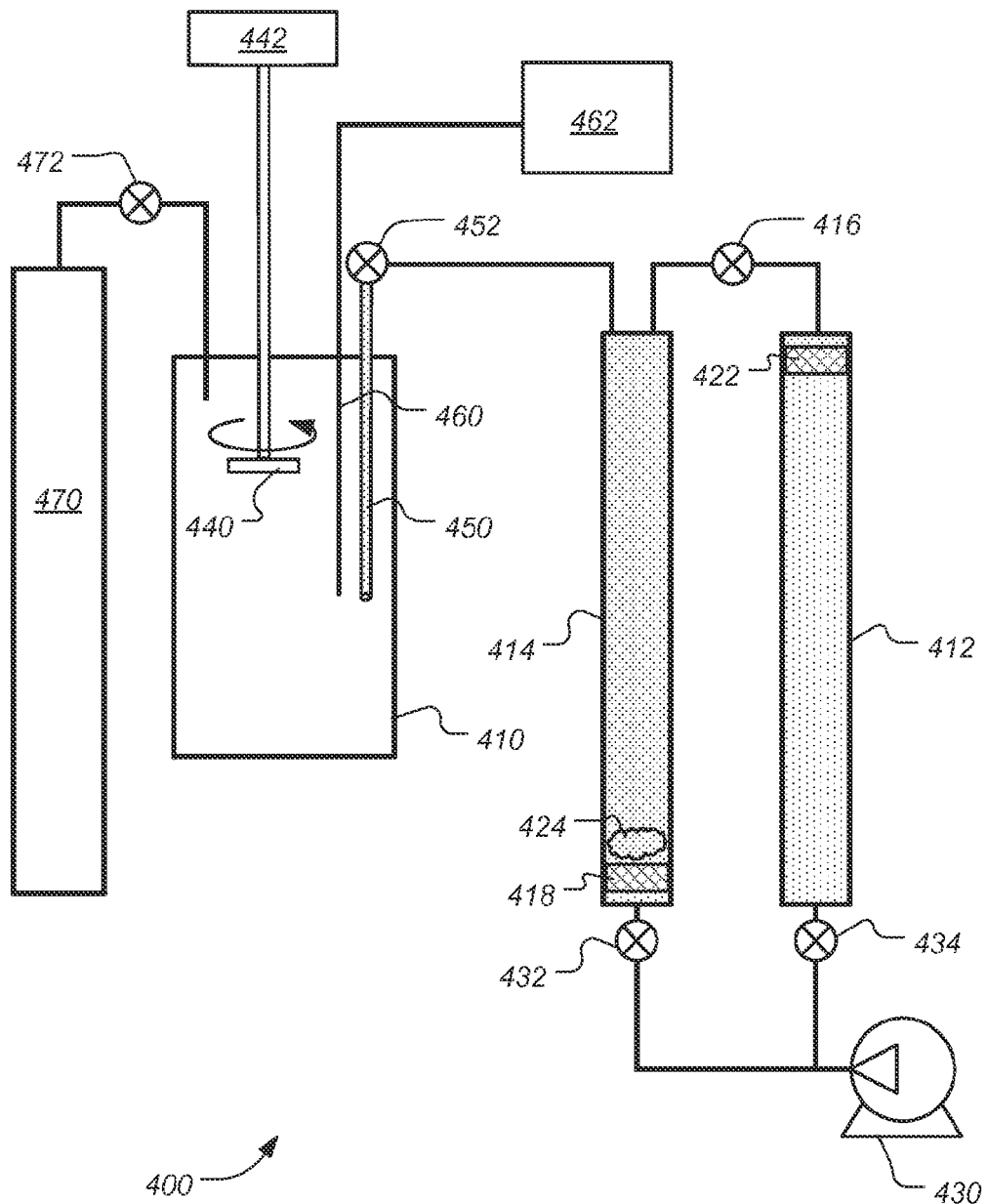
Figure 6:
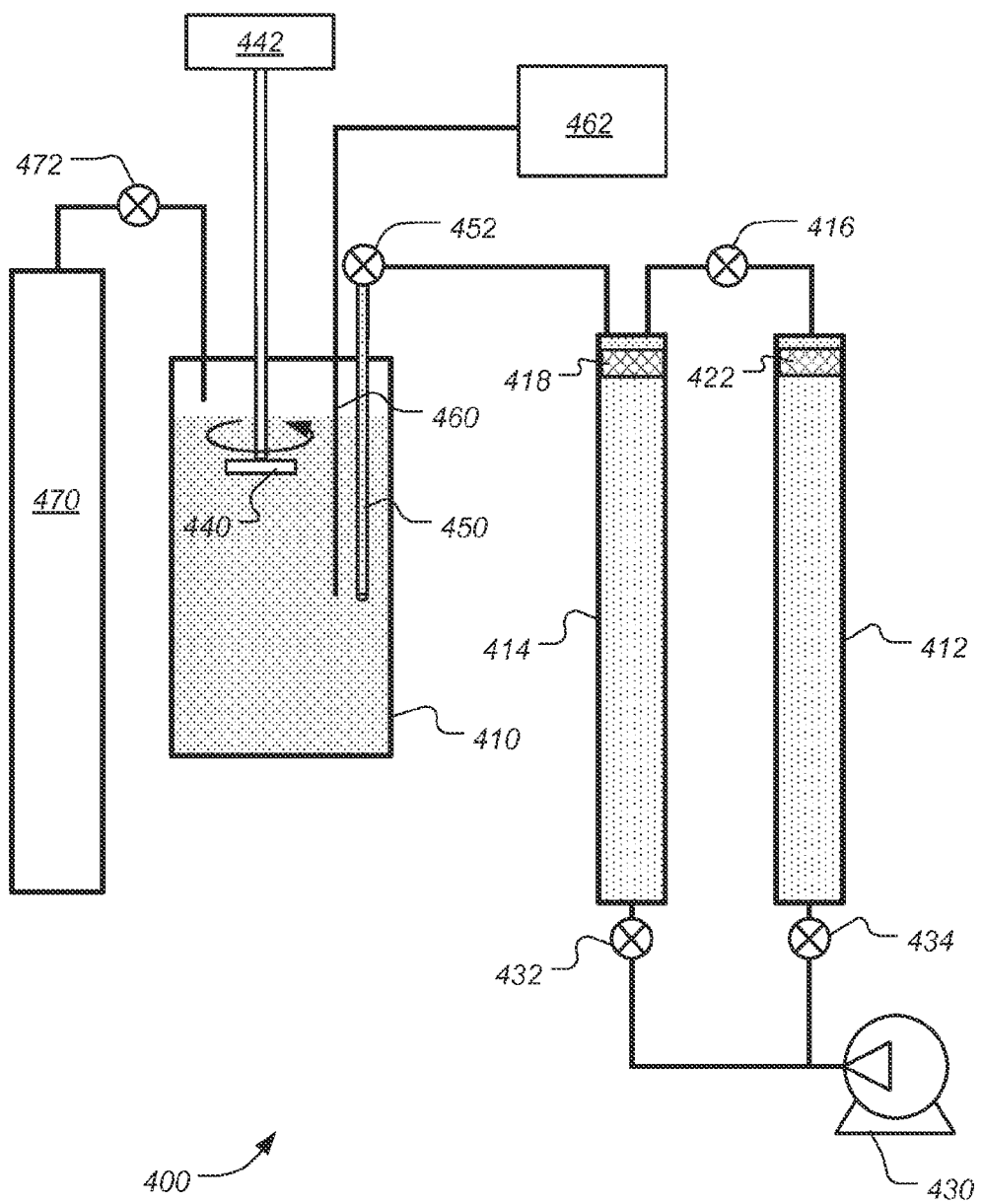

FIGS. 4-6 are block diagrams illustrating operational aspects of a system for estimating diffusion coefficients for a reservoir stimulation fluid, according to some other embodiments. The operation of testing system 400 is similar to that of system 100 shown in FIGS. 1-3, except that the spent acid is generated in a separate chamber 414 rather than in the reaction vessel 410. FIG. 4 shows the fresh acid in fresh acid accumulator 412. The carbonate powder 424 (or other material) is measured and placed in spent acid accumulator 414. In FIG. 5, the fresh acid is moved from the fresh acid accumulator 412 to the spent acid accumulator 414 using a combination of pumping with pump 430 and valves 434 and 416. In particular, piston 422 is moved upwards under pressure from pump 430 and valve 434 while valve 416 is opened, allowing the fresh acid in accumulator 412 to move into accumulator 414. The acid is thus allowed to react with the carbonate powder 424 in accumulator 414. According to some embodiments, the pressure within accumulator 414 is controlled using the pump 430 and valve 432. The temperature can also be controlled using heating jackets (not shown). The reaction in accumulator 414 is carried out and results in a spent acid containing weakened acid as well as the by-products of the reaction. The reaction can be aided with a magnetic mixing pin such as shown in FIGS. 1-3, or other agitation means. After formation of the spent acid in accumulator 414, the spent acid is transferred to the reaction vessel 410 under action of the pump 430 and valves 432 and 452, and injection tube 450. According to some embodiments, the vessel 410 is pressurized with a nitrogen backpressure system that includes gas source 470 and valve 472. As in the case of system 100 shown in FIGS. 1-3, according to some embodiments, pressures of 1000 psi, 3000 psi, 5000 psi and/or even 10,000 psi are used for carrying out the tests in vessel 410. FIG. 6 shows the system 400 with the spent acid in the vessel 410, which is free to react with the material on the rotating disk 440 being driven by motor system 442. As in the case of system 100, a thermocouple 460 is provided for measuring and/or controlling the temperature within the reaction vessel 410.

Figure 7:
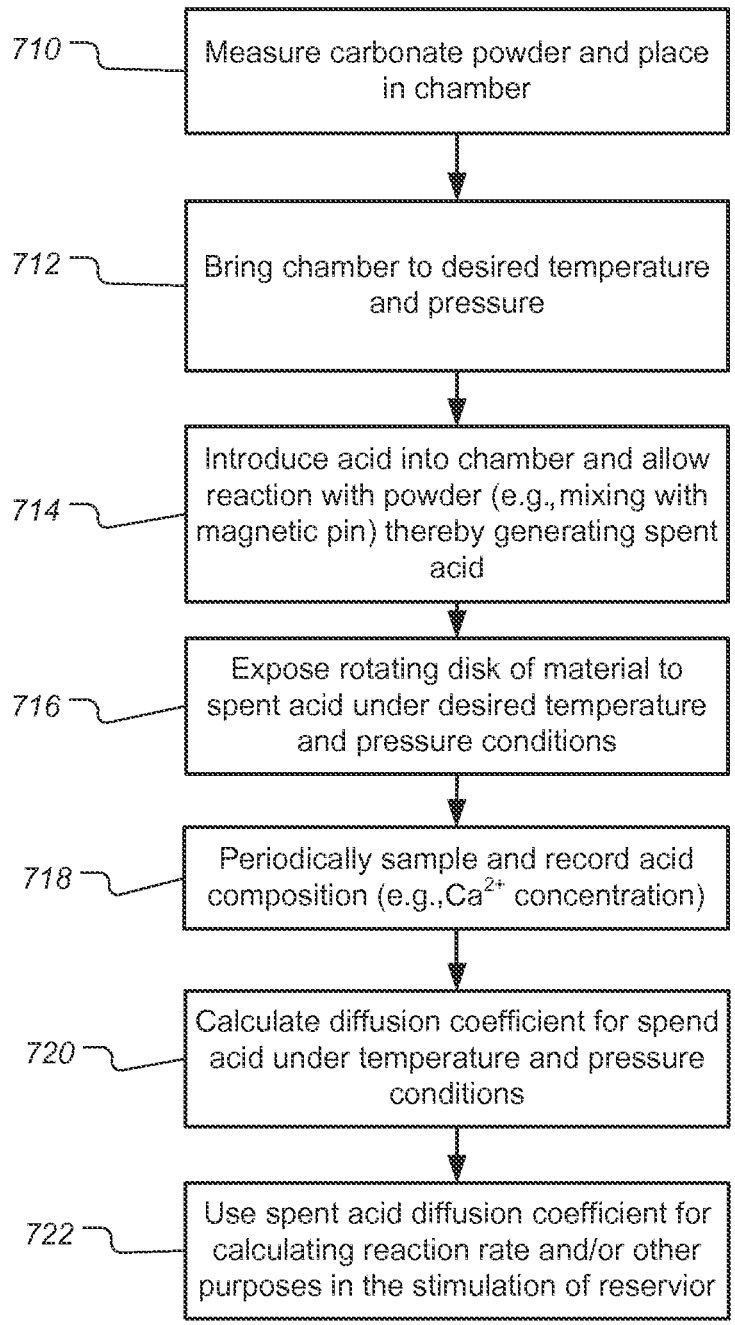
FIG. 7 is a flow chart illustrating aspects of estimating diffusion coefficients for reservoir stimulation fluids, according to some embodiments.

FIG. 7 is a flow chart illustrating aspects of estimating diffusion coefficients for reservoir stimulation fluids, according to some embodiments. In block 710, the carbonate powder is measured and placed in the chamber used to form the spent acid. In systems such as system 100 of FIGS. 1-3, this is the reaction vessel. In systems such as system 400 of FIGS. 4-6 this is a separate accumulator used for generating the spent acid. The quantity of carbonate material can be calculated depending on the desired characteristics of the test, as described above. Note that in the case of stimulation of non-carbonate reservoir formations, or in the case of non-acid stimulations (e.g., such as chelating agents), other material is used as a reactant to generate the spent acid (or spend stimulation fluid). In block 712, the chamber is stabilized to a desired temperature and pressure. In block 714, fresh acid is introduced into the chamber to allow reaction with the carbonate powder. The reaction can be facilitated, for example using a magnetically driven mixing pin or other means. When the spent acid has the desired characteristics, in block 716 the spent acid is introduced or allowed to contact (depending on the type of system) the rotating disk of carbonate material. According to some embodiments, the disk is solid marble. The temperature and pressure of the reaction vessel is controlled to match that of expected downhole conditions, or other desirable levels for the experiment. In block 718, the acid composition is periodically sampled and analyzed (e.g., for $Ca^{2+}$ concentration in the case of spent acid for carbonate reservoirs). In block 720, the spent acid measurements are used to calculate the diffusion coefficient for the particular spent acid under the particular temperature and pressure conditions. In block 722, the calculated diffusion coefficient is used to calculate the reaction rate or for other purposes in planning and/or executing a stimulation job in the field. According to some embodiments, the spent acid diffusion coefficient is used in a modeling technique such as discussed in co-owned U.S. patent application Ser. No. 13/752859, filed Jan. 29, 2013, entitled "Method for quantitative prediction of matrix acidizing treatment outcomes," which is incorporated by reference herein.

According to some embodiments, the techniques described herein are used for deriving diffusion coefficients for other acids or stimulation fluids besides spent HCl acid for carbonate reservoirs. For example, in the case of acid stimulation of sandstone reservoir formations, HF acid or a combination of HCl and HF can be used. In this case, other material can be used (1) for generating the spent acid and (2) for the rotating disk material. Examples of acids for other types of stimulation from which "spent" acids can be formulated and used for testing include: (1) organic acids, such as acetic acid, formic acid; (2) combinations of HCl and organic acid(s); (3) chelating agents; (4) emulsified acid; and (5) gelled acid. In each case the spent acid is formed, including one or more by-products of reaction with the intended reaction material, at the temperature and pressure conditions expected downhole. The resulting diffusion coefficient and reaction rate information can then be used instead of, or in addition to, the diffusion coefficients and reaction rate information for fresh acid (or other fluid).

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. §112, paragraph 6 for any limitations of any of the claims herein, except for those in which the claim expressly uses the words 'means for' together with an associated function.

What is claimed is:

1. A method of estimating a diffusion coefficient for a stimulation fluid used to stimulate a subterranean reservoir rock by at least partially dissolving the rock, the method comprising:
   generating a partially spent stimulation fluid comprising a stimulation fluid used to stimulate the subterranean reservoir rock and one or more reaction by-products, the reaction by-products being of a type produced during reaction of the stimulation fluid with the reservoir rock;
   in a sealed chamber, exposing a sample of reactant material to the partially spent stimulation fluid under elevated pressure conditions such that the reactant material reacts with the partially spent stimulation fluid; and
   measuring properties of the partially spent stimulation fluid after at least some of the reactant material has reacted with the partially spent stimulation fluid and estimating therefrom a diffusion coefficient for the stimulation fluid under partially spent downhole conditions.

2. A method according to claim 1, wherein the reservoir rock is a carbonate reservoir rock and the reaction by-products includes dissolved $CO_2$.

3. A method according to claim 2, wherein the reaction by-products further includes calcium ions.

4. A method according to claim 2, wherein the reaction by-products further includes magnesium ions.

5. A method according to claim 1, wherein the sample of reactant material is a solid rotating disk having a material found in the subterranean reservoir rock.

6. A method according to claim 5, wherein the subterranean reservoir rock is carbonate, the solid rotating disk is marble and the stimulation fluid includes hydrochloric acid.

7. A method according to claim 1, wherein exposing the sample of reactant material with the partially spent simulation fluid is performed under elevated temperature conditions.

8. A method according to claim 7, wherein the elevated pressure and elevated temperature conditions correspond to temperature and pressure conditions expected in the subterranean reservoir rock.

9. A method according to claim 1, wherein the elevated pressure is at least 1000 psi.

10. A method according claim 9, wherein the elevated pressure is at least 3000 psi.

11. A method according to claim 1, wherein the subterranean reservoir is a carbonate reservoir, and the partially spent stimulation fluid is generated by reacting HCl with $CaCO_3$.

12. A method according to claim 1, further comprising estimating a reaction rate based at least in part on the estimated diffusion coefficient.

13. A method according to claim 1, further comprising modeling wormhole morphology based at least in part on the estimated diffusion coefficient.

14. A method according to claim 1, wherein measuring properties of the partially spent stimulation fluid includes sampling the partially spent stimulation fluid at intervals while the reactant material reacts with the partially spent stimulation fluid.

15. A method according to claim 1, wherein the stimulation fluid includes one or more of the following selected from a group consisting of: hydrochloric acid; organic acids; chelating agents; emulsified acid; and gelled acid.

* * * * *